United States Patent [19]

Kramer et al.

[11] Patent Number: 4,850,729
[45] Date of Patent: Jul. 25, 1989

[54] DECONTAMINATING COMPOSITION AND DELIVERY SYSTEM THEREFOR

[75] Inventors: David N. Kramer, 2119 Wiltonwood Rd., Stevenson, Md. 21153; Philip A. Snow, Henderson, Md.

[73] Assignee: David N. Kramer, Stevenson, Md.

[21] Appl. No.: 35,386

[22] Filed: Apr. 7, 1987

[51] Int. Cl.$^4$ .............................................. A46B 11/00
[52] U.S. Cl. ...................................... 401/183; 401/186; 401/287; 401/288; 252/106; 252/186.29; 423/272; 423/273
[58] Field of Search ............... 401/196, 183, 132, 145, 401/143, 151, 156, 270, 271, 273, 278, 286, 186, 287, 288; 206/219, 221; 215/DIG. 8; 423/272; 252/186.29

[56] References Cited

U.S. PATENT DOCUMENTS

| | | | |
|---|---|---|---|
| 1,332,985 | 3/1920 | Jarrett | 401/132 |
| 2,956,570 | 10/1960 | Stanford | 401/270 |
| 3,167,057 | 1/1965 | Bross | 401/151 |
| 3,240,328 | 3/1966 | Matteuzzi | 206/219 |
| 3,486,504 | 12/1969 | Austin | 401/132 |
| 3,741,383 | 6/1973 | Wittwer | 206/219 |
| 3,756,389 | 9/1973 | Firth | 206/219 |
| 3,797,646 | 3/1974 | Horne | 206/219 |
| 3,964,643 | 6/1976 | Morane et al. | 206/219 |
| 3,986,974 | 10/1976 | Loffelman et al. | 423/272 |
| 4,008,968 | 2/1977 | Hobbs | 401/183 |
| 4,017,411 | 4/1977 | Diehl et al. | 252/186.29 |
| 4,086,177 | 4/1978 | Kubitschek et al. | 423/272 |
| 4,120,652 | 10/1978 | Scholer et al. | 252/186.29 |
| 4,141,850 | 2/1979 | Readio et al. | 252/186.29 |
| 4,145,305 | 3/1979 | Demarcq et al. | 423/272 |
| 4,193,698 | 3/1980 | Gartner | 206/219 |
| 4,362,241 | 12/1982 | Williams | 401/132 |
| 4,397,757 | 8/1983 | Bright et al. | 252/186.29 |
| 4,594,015 | 6/1986 | Pomares | 401/183 |

FOREIGN PATENT DOCUMENTS

| | | | |
|---|---|---|---|
| 113506 | 9/1980 | Japan | 252/186.29 |
| 7601512 | 8/1976 | Netherlands | 252/186.29 |

*Primary Examiner*—John Doll
*Assistant Examiner*—Wayne A. Langel
*Attorney, Agent, or Firm*—Leonard Bloom

[57] ABSTRACT

A decontaminating composition and delivery system therefor. The decontaminating composition is prepared by combining a "per-salt", an activator for hydrogen peroxide which effects free radical formation, both of which are in a dry form and an aqueous solution comprised of a nonvolatile alcohol and a surface active agent. The "per-salt" of the present invention is a basic water-soluble salt such as percarbonate, perborate, persilicate or perphosphate which releases hydrogen peroxide in aqueous solution. While not true per-salts in the strict chemical sense, they are otherwise conventional salts containing hydrogen peroxide of crystallization which is released in aqueous solution. The decontaminating composition and delivery system comprise a dispenser containing, in separate compartments, the various components as aforesaid which are thoroughly mixed prior to being dispensed onto the surface to be treated.

31 Claims, 4 Drawing Sheets

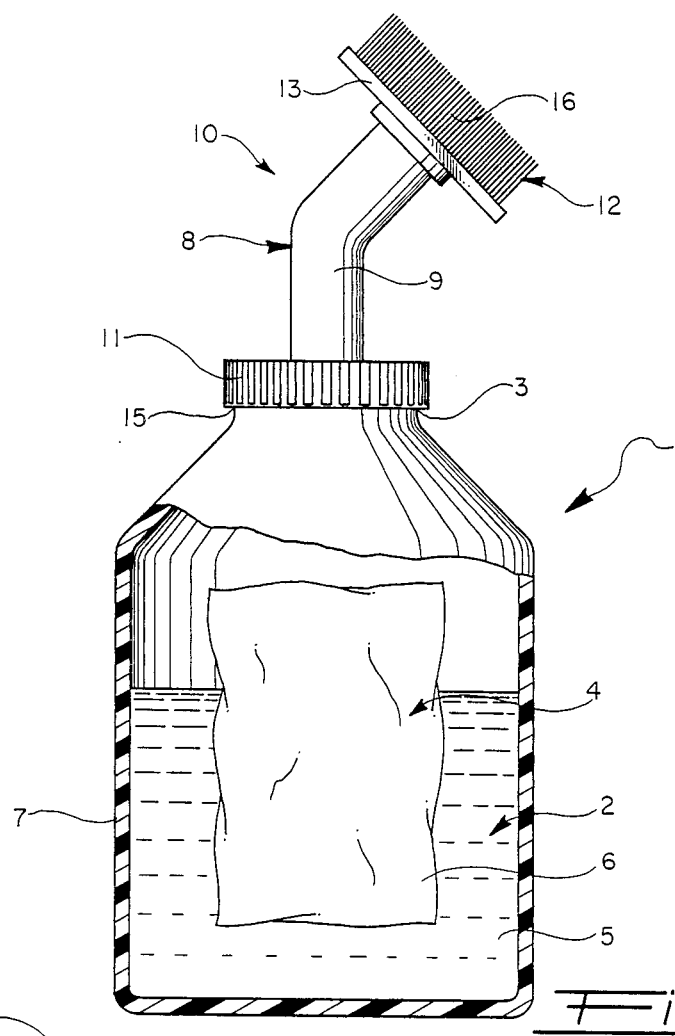
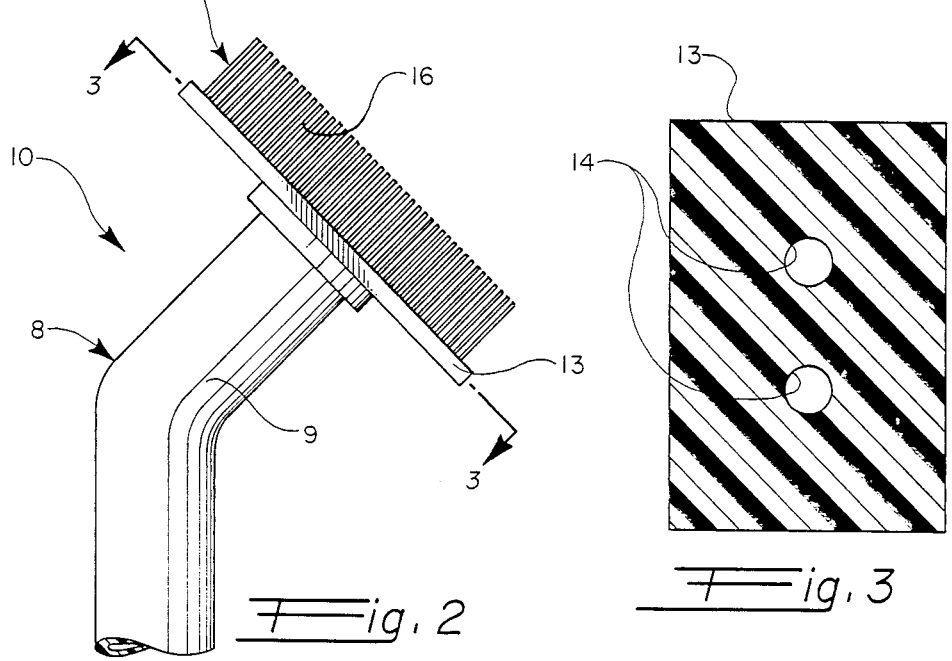 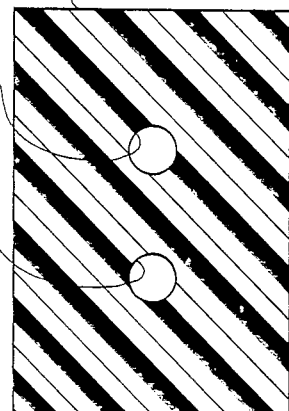

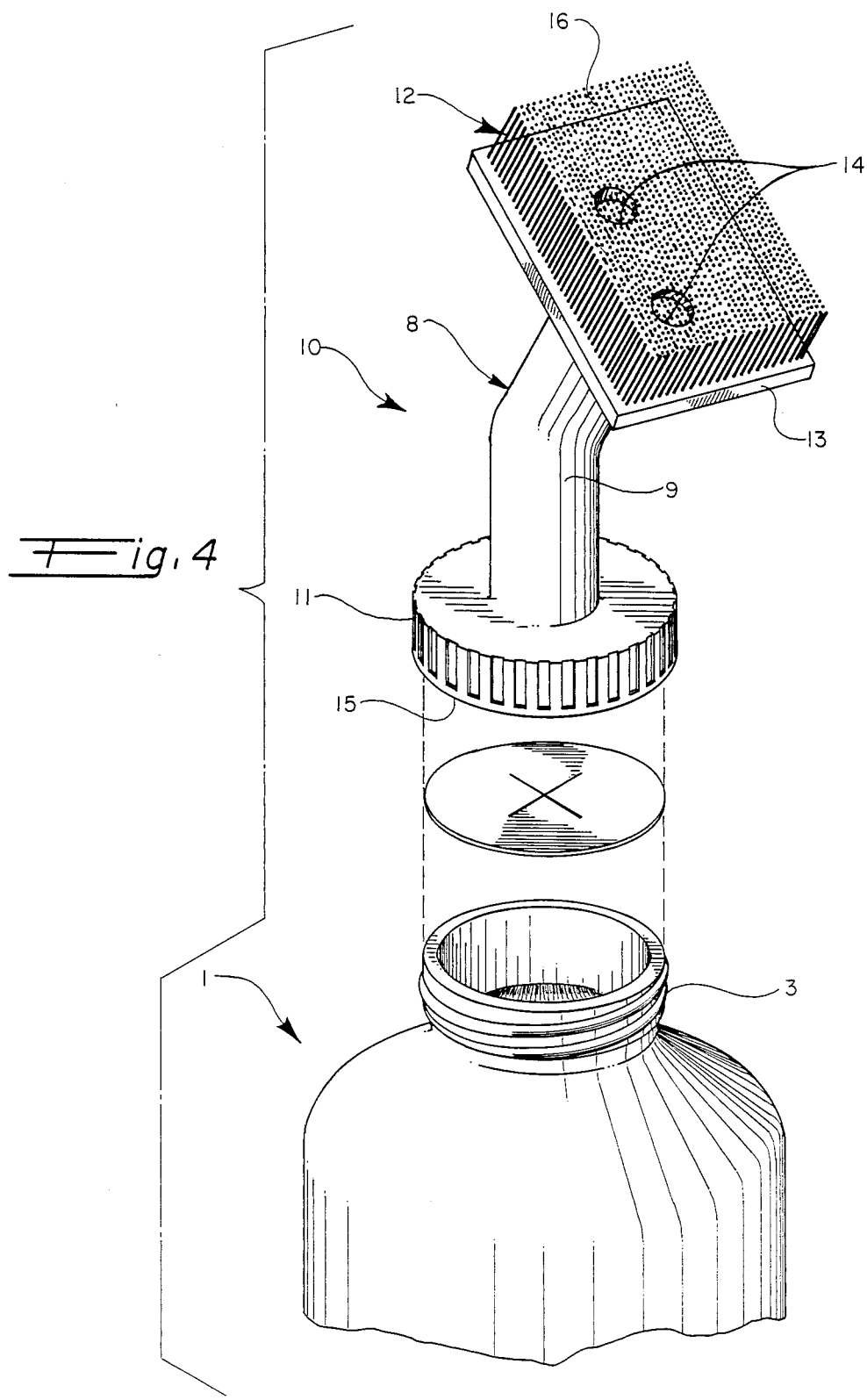

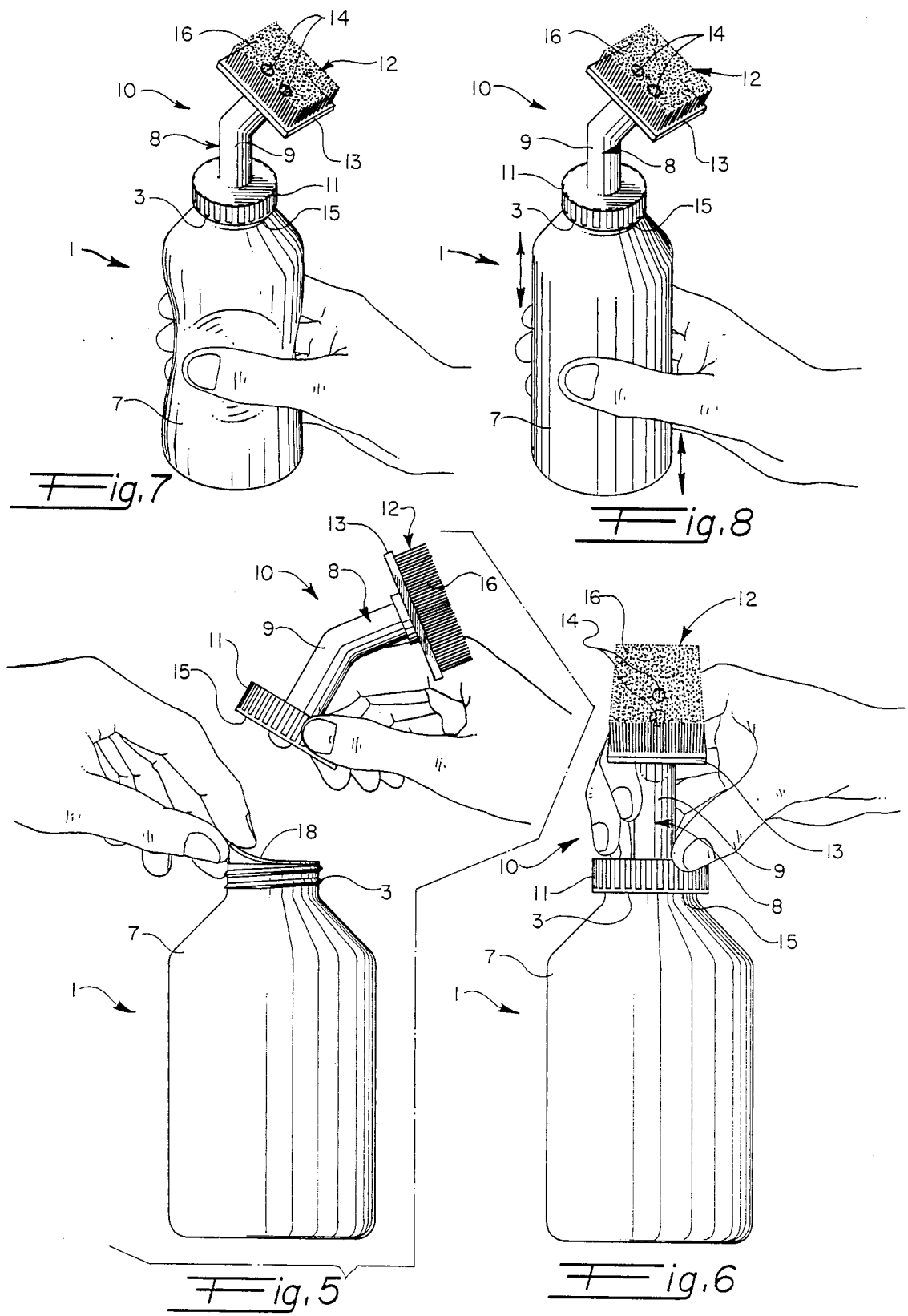

und delivery systems therefor
DECONTAMINATING COMPOSITION AND DELIVERY SYSTEM THEREFOR The invention described herein was made under a contract or award from the Department of Defense.

FIELD OF THE INVENTION

The present invention relates to compounds for decontaminating purposes and delivery systems therefor and in particular to chemical decontaminant compositions and a system for storing and delivering the said compositions.

BACKGROUND OF THE INVENTION

Presently, water washdown is the mode used to effect clean-up of chemical spills and of chemical warfare agents which contaminate exterior surfaces. Where non-persistent agents are involved such a washdown, with additional subsequent evaporation and degradation by natural processes (such as interaction with the environment, heat and surfaces) will, with time, clear the area of contamination. However, where persistent agents, enclosed areas, (especially those that house sensitive electronic equipment) and/or contaminated personnel are involved, specialized decontamination methods and materials must be employed.

Examples of standard chemical decontaminants for toxic substances are compositions containing diethylenetriamine, supertropical bleach (STB) and phenolic solutions, such as sodium phenolate. In addition to the foregoing, other substances such as ammonia, sodium hydroxide, sodium carbonate, lime, sodium hypochlorite and trisodium phosphate may be used as decontaminating agents. Heat, soapy water, Fullers' earth and steam may also be used as decontaminants in certain situations.

The use of compositions containing chlorinating agents as decontaminating agents (i.e., supertropical bleach, sodium hypochlorite, etc.) have a number of drawbacks. First, they are extremely corrosive. In addition, they are a potent irritant. Also, and perhaps most importantly, there is a significant vapor hazard associated with the chlorine generated by such agents. Indeed, exceeding the maximum permissible concentration of 3 mg./m$^3$, or 1.5 mg./m$^3$ of chlorine as a gas at standard temperature and pressure for fifteen minutes, can result in severe respiratory tract damage. Consequently, when chlorinating agents are employed in either enclosed areas or on personnel, the use of gas masks, special protective gear and the presence of adequate ventilation is required.

Disadvantages associated with the use of compositions containing diethylenetriamine are that, although they react with both the nerve agents and blister agents present in many chemical contaminants thereby effectively removing the hazards presented by the contaminant, within approximately five minutes, personnel performing the decontamination must be masked because of its own vapor generated and rubber gloves must be worn to protect the hands. Thus, it is unsuitable for decontaminating personnel. In addition, diethylenetriamine is partially corrosive, is an effective paint remover, and is combustible, resulting in fires when brought in contact with supertropical bleach (STB). Accordingly, its very properties preclude its use in enclosed areas especially when sensitive electronic equipment is housed therein.

For the effective decontamination of clothing, hard surfaces and sensitive electronic equipment, it is necessary to solubilize, disperse and homogenize deposits of the contaminating agent in order to provide rapid and intimate contact with the chemical decontaminating reagents. The possible use of thickened contaminating agents and the penetration of the contaminating agents in grease, oil, soils and porous surfaces require that the decontaminating system have detergents, dispersants and a means of physically brushing the decontaminating reagents onto the surface to be treated. In the decontamination of equipment that is sensitive to corrosion, non-corrosive decontaminants must be employed. Also, the toxicity of the decontaminating reagents must be of a low order in cases where it is to be applied to clothing and directly to contaminated personnel.

In the use of any reliable decontaminating system and procedure, one must assume that the worst set of circumstances possible exist. For example, a contaminating agent which, based of its volatility, is classified as non-persistent, may become persistent by virtue of several occurrences such as its dissolution in water or by its incorporation into films, soils and thickening agents. Thus, it must always be assumed that the contaminant involved has, if possible, become persistent and "clean up" thereof must proceed accordingly.

Assuming that an effective chemical decontaminating agent is employed, it is also necessary that the reactants, (i.e., contaminating agent and decontaminant) be brought together in intimate and homogeneous contact with one another. Otherwise, such as is the case where mustard gas is involved, a shell forms around the mustard globule preventing the decontaminent from further reacting therewith. Accordingly, a system which prevents formation of such globules and provides this effective solubilization and homogeneous contact is required.

A means is also required for effectively and safely dispensing and applying the decontaminating chemicals by relatively untrained personnel who may also become contaminated by contact therewith. Further, the decontaminating system must not impose a logistical burden, but rather, it must be able to rapidly deployed and must be readily available for use without requiring excessive manipulation.

Ideally, the decontaminating system must also be thermally stable, efficacious, noncorrosive and operable at temperature extremes. Moreover, the system should not present any hazards to the user and the environment.

SUMMARY OF THE INVENTION

The decontaminating composition and delivery system of this invention finds utility in decontaminating surfaces, clothing and personnel that have been contaminated with corrosive and/or toxic substances. Such situations arise, for example, in the event of spills of chemicals, pesticides and other chemical agricultural compositions, as well as in the event of chemical warfare. The decontaminating composition of the present invention is prepared by combining a "per-salt", an activator for hydrogen peroxide which effects free radical formation (i.e., clay), a positively charged phase-transfer agent and an aqueous solution comprised of a nonvolatile alcohol and a surface active agent. As used herein, the term "per-salt" is used to refer to an alkaline water-soluble salt which releases or forms hydrogen peroxide when in aqueous solution. The compounds embraced in this definition may not be true per-salts in the strict chemical sense but; rather, are otherwise conventional salts containing hydrogen peroxide of crystallization which is released in aqueous solution. In order to insure long shelf life, the above enumerated components are combined just before use. The full decontaminating system of the invention comprises a dispenser containing, in various compartments, the components which components are thoroughly mixed prior to being dispensed onto the surface to be treated.

The decontaminating system of the present invention, comprising the decontaminating composition and the delivery system therefor, is low in cost. Moreover, the decontaminating composition is characterized by its effectiveness, low toxicity, low corrosivity and the ready availability of its constituent components. The latter is particularly advantageous when decontaminating clothing and sensitive electronic equipment.

It is therefore a primary object of the present invention to provide a composition and a delivery system therefor for the effective decontamination of surfaces exposed to toxic and corrosive materials as a result of chemical warfare.

It is therefore an object of this invention to provide a composition, and a delivery system therefor, for the effective decontamination of surfaces exposed to toxic and corrosive materials.

It is another object of this invention to provide a nontoxic composition and a delivery system therefor for the decontamination of surfaces exposed to toxic and corrosive materials.

It is still another object of this invention to provide a noncorrosive composition, and a delivery system therefore, for the decontamination of surfaces exposed to toxic and corrosive materials.

It is yet another object of this invention to provide a composition, and a delivery system therefor, for the decontamination of surfaces exposed to toxic and corrosive materials, which composition is comprised of readily-available components.

Still another object of this invention is to provide a decontaminating system that is readily used without excessive manipulation by relatively untrained personnel.

Still another object of this invention is to provide a low cost decontaminating system.

Yet other objects will be apparent to those skilled in the art.

The foregoing and other objects are accomplished by the practice of this invention. Broadly, viewed in one of its principal aspects, this invention consists of a composition for decontaminating surfaces exposed to toxic and corrosive materials, wherein said composition consists of a combination of:

(1) a water-soluble basic salt having hydrogen peroxide of crystallization; (2) an activator for hydrogen peroxide which effects free radical formation; (3) a positively-charged phase transfer agent; and (4) an aqueous solution comprised of a nonvolatile alcohol and a surface active agent, wherein said components are combined and thoroughly mixed just prior to use.

The practice of the invention is implemented in a decontaminating system which includes a pliable bottle. A spreading means is removably affixed to the mouth of the bottle. Said spreading means is in open communication with the contents of said bottle. Said bottle contains, in various separate compartments therein, a water-soluble basic salt having hydrogen peroxide of crystallization, an activator for hydrogen peroxide which effects free radical formation, a positively-charged phase transfer agent, and an aqueous solution of a nonvolatile alcohol and a surface active agent. The interface between the various separate compartments is ruptured, so as to allow the components to become thoroughly mixed prior to dispensing the mixture through the mouth of the bottle where it may be spread by the spreading means over a surface to be decontaminated.

The instant invention thus provides a decontaminating system comprising a dispenser containing a decontaminating composition. The decontaminating composition is a combination of a water-soluble basic salt having hydrogen peroxide of crystallization, an activator for hydrogen peroxide which effects free radical formation, a positively-charged phase transfer agent and an aqueous solution of a nonvolatile alcohol and a surface active agent. In order to enhance shelf life of the decontaminating composition, components are contained within separate compartments in the dispenser so that the incompatible aqueous vehicle is chemically separated from the per-salt, and are combined and mixed only just prior to use. The composition is then dispensed through the mouth of the dispenser, which is fitted with a brush or other spreading means, and is thereby spread over a surface to be decontaminated.

In accordance with the teachings of the present invention a system is disclosed for delivering a decontminating composition having compatible dry components and compatible liquid components. Said delivery system includes a bottle having pliable walls. The bottle further has an internal reservoir portion, and a mouth portion. Spreading means provides for receiving the composition exiting from the bottle through the mouth portion thereof. Spreading means further provides for spreading the received composition onto a surface in need thereof. At least one chamber is disposed in the internal reservoir portion of the bottle. Said chamber has frangible walls. Wherein, compatible dry componets of the decontaminating composition are disposed within the chamber, and further wherein compatible liquid components are disposed in the internal reservoir portion. Preferably the mouth portion is threaded. Also preferably, the mouth portion is of reduced cross-section. In another preferred embodiment, the spreading means includes a cap portion. This cap portion is received over the mouth portion of the bottle. Said cap portion has at least one aperture formed therein. Said spreading means further includes a spreading portion. Preferably the spreading portion includes brush hairs for spreading the composition onto a surface in need thereof. Alternatively, the spreading portion includes an absorbant material for spreading the composition onto a surface in need thereof.

In another preferred embodiment, there is provided an adapter having a neck. One end of said neck is received over and secured to the mouth portion of the bottle. Said neck further has a second end being secured to and in fluid communication with the spreading means, such that the composition may flow, respectively, through the mouth portion of the bottle and the neck of the adapter to be received in the spreading means. Preferably this system further includes a cap portion positioned at the one end of the neck for being received over and secured to the mouth portion of the bottle. Said cap portion has an aperture formed therein such that the composition may flow from the bottle into the neck of the adapter through respectively, the mouth portion of the bottle and the cap portion. The spreading means further includes lateral wall positioned at the second end of the neck of the adapter. The lateral wall has at least one aperture formed therein, and further having the spreading portion disposed thereon, such that the composition in the neck of the adaptor is in fluid communication with the spreading portion being received thereon for spreading the composition on a surface in need thereof. Also preferably, the mouth portion of the bottle is threaded and the cap portion is threaded for threadably engaging the said threads of the mouth portion, thereby securing said cap to said mouth portion. Also preferably, the neck of the adaptor is curved.

In further accordance with the teachings of the present invention, the system further includes a self-sealing valve positioned over the mouth portion of the bottle for controlling the flow of the composition therethrough. In a preferred embodiment, the self-sealing valve is comprised of a rubber disc having a pair of intersecting cross-hair gaps formed therein.

The nature and substance of the present invention as well as its objects and advantages will be more clearly perceived and fully understood by referring to the following description and claims taken in connection with the accompanying drawings which are described briefly below.

BRIEF DESCRIPTION OF THE DRAWINGS

FIG. 1 depicts the squeeze bottle dispenser delivery system of the invention with part thereof in section to show the separate compartments, two of which are frangible pouches, each of which contain respective components of the decontaminating composition.

FIG. 2 is an enlarged view of a portion of the dispenser of FIG. 1 showing the cap partially in section and partially in elevation.

FIG. 3 is a section view through the cap taken along lines 3—3 of FIG. 2.

FIG. 4 is an exploded view of the cap of FIG. 2.

FIG. 5 illustrates removal of the seal from the mouth of the squeeze bottle dispenser of FIG. 1 after removal of the cap therefrom.

FIG. 6 depicts the cap being replaced on the mouth of the squeeze bottle dispenser after removal of the seal therefrom.

FIG. 7 depicts the squeeze bottle dispenser of FIG. 1 being squeezed to thereby rupture the interface which separates the components of the decontaminating composition.

FIG. 8 shows the dispenser of FIG. 1 being kneaded and shaken to mix the components of the decontaminating composition.

FIG. 12 depicts the squeeze body dispenser delivering system of the present invention, with parts thereof broken away and sectioned, to show the stirring bar for mixing.

FIG. 13 depicts the squeeze body dispenser delivering system of the present invention, with parts thereof broken away and sectioned, to show the marble for mixing.

DESCRIPTION OF THE PREFERRED EMBODIMENTS

The decontaminating composition and the dispensing system therefor of this invention are characterized by a number of advantages over the prior art. The decontaminating composition is effective, nontoxic, noncorrosive and is comprised of readily-available components. The decontaminating system of the invention, comprising the decontaminating composition and dispenser therefor, has a long shelf life and is readily used without excessive manipulation, even by relatively untrained personnel.

Figure 9:
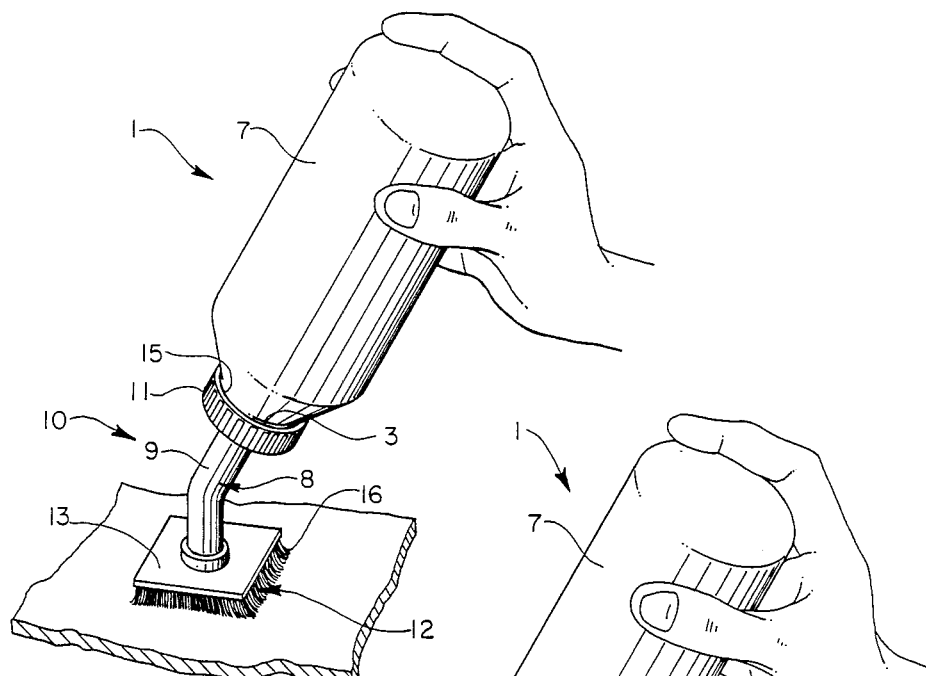
FIG. 9 shows the contents of the squeeze bottle dispenser being applied to a surface to be decontaminated.
Figure 10:
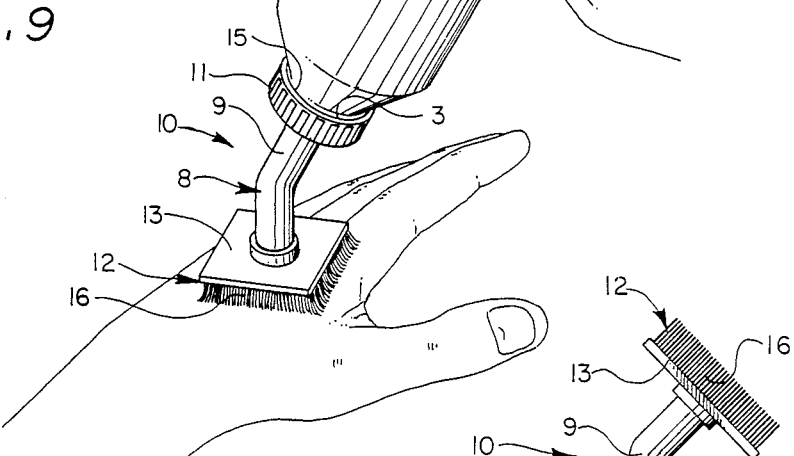
FIG. 10 illustrates a subject applying the decontaminating composition of the invention from the dispenser onto his left hand.

The decontaminating composition is derived from a water-soluble basic salt having hydrogen peroxide of crystallization, an activator for hydrogen peroxide which effects free radical formation, a positively-charged phase transfer agent and an aqueous solution comprised of a nonvolatile alcohol and a surface active agent. In order to prolong shelf life, incompatible components of the decontaminating composition are contained in separate compartments in the dispenser (FIGS. 1 and 11) and are combined and mixed just prior to use (FIGS. 5–10). The resultant decontaminating composition, comprising an aqueous solution of the basic salt containing hydrogen peroxide of crystallization, the nonvolatile alcohol and the surface active agent and having the activator dispersed therein, is then dispensed through the mouth of the dispenser, which is fitted with a brush or other spreading means, and is thereby spread over a surface to be decontaminated (FIGS. 9 and 10).

The salt used in the practice of this invention may be any water-soluble basic salt which has hydrogen peroxide of crystallization or which produces $H_2O_2$ upon dissociation. Examples of suitable classes of per-salts are soluble perborates, persilicates, perphosphates and percarbonates associated with a suitable cation, including various mixtures thereof. The preferred cations are alkali metals such as lithium, sodium and potassium and alkaline earth metals such as calcium and barium. Especially preferred is sodium percarbonate having an empirical formula of $2 Na_2CO_3 \cdot 3H_2O_2$. Sodium percarbonate is a white granular powder with an available oxygen content of 13% by weight. Its solubility in water is 140g./1. at 24° C. and 1% by weight solution has a pH of 10.5. It dissolves rapidly in water, is odorless and is noncorrosive. However, it does react slowly with galvanized steel and aluminum to form essentially inert oxide films thereon.

There are a number of activators for hydrogen peroxide which effect free radical formation. Examples of these activators are peroxidase, iron chelates, ultraviolet light, ketones, organic esters, nerve agents such as organic phosphonates, and iron bearing clays such as attapulgite, bentonite, kaolinite, montmorillonite, and Christiana clay (which is predominately kaolinite) as well as mixtures thereof. The preferred activators are the iron bearing clays as well as various mixtures thereof. An advantage of using clay as a hydrogen peroxide activator in the decontaminating compositions of this invention is that, when the components are mixed prior to use, the clay acts as a thickening agent forming the decontaminating composition in a cream form. In addition to increasing the viscosity of the decontaminating composition, clay has advantageous rheological properties and it is an absorber for organics for forming a reaction site.

Clays are preferred. If an activator other than clay is utilized, the resulting decontaminating composition will be more in the form of a solution than a cream. In such a case, the addition of viscosity builders such as methyl cellulose may be incorporated to thicken or gel the solution.

Preferably, both the per-salt and the clay are in the form of dry components.

Of the dry components of the decontaminating composition, by weight about 15 percent to about 85 percent of the total of said dry components is the per-salt, with a preferred range being about 25 percent by weight to about 75 percent by weight of the per-salt and with approximately 40% by weight being the most preferred. The clay content of the total of said dry components may vary from about 15 percent by weight to about 85 percent by weight, with about 25 percent by weight to about 75 percent by weight being preferred and with approximately 60% by weight being the most preferred. In an especially preferred composition, the dry components are comprised of 40 percent by weight of sodium percarbonate, 24 percent by weight of attapulgite and 30 percent by weight of kaolinite and 6 percent by weight bentonite.

The positively charged phase-transfer agent may be a phosphonium salt such as t-butyl phosphonium iodide, a sulfonium salt such as tributyl sulfonium chloride, or a quaternary ammonium salt. The choice of the positively charged p.hase-transfer agent is critical. The choice of the counter anion of the positively charged phase-transfer agent is not critical in this regard. The hydrocarbyl groups attached to the phosphorous, sulfur or nitrogen must contain a total number of carbons, such that the compound is water-soluble but yet has sufficient lipophilic character to permit it to pass from the aqueous phase into a non-polar oil (or organic) phase. The compounds become disinfecting as they become lipophilic.

The preferred positively charged phase-transfer agents are quaternary ammonium salts having a chain of carbon atoms of ca. 6 to 30, and preferably ca. 8 to 25, in length on the quaternary nitrogen. The number of carbons on the nitrogen of the quaternary ammonium salt, as mentioned, is critical. The quaternary ammonium salt must not only be water-soluble, but it must also possess sufficient lipophilic character to permit it to pass from the aqueous phase into an oil (or organic) phase. When the salt containing hydrogen peroxide of crystallization is dissolved in an aqueous solution containing a positively charged phase-transfer agent, such as a quaternary ammonium salt, the salt extracts a proton from the hydrogen peroxide, leaving the negatively charged hydroperoxide ion. The hydroperoxide ion then becomes associated with the quaternary ammonium ion and its negative charge is effectively neutralized:

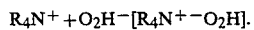
$$R_4N^+ + O_2H^- [R_4N^+ {}^-O_2H].$$

The resultant lipophilic quaternary ammonium hydroperoxide may then pass from the aqueous phase into an oil, or organic phase where the hydroperoxide ion may exert its disinfecting and decontaminating effects. While quaternary ammonium salts are disinfectants and decontaminants themselves, these properties are enhanced synergistically when they are combined with a per-salt.

In the practice of this invention, a single positively charged phase-transfer agent or a mixture of positively charged phase-transfer agents may be used. Particularly suitable positively charged phase-transfer agents are didecyl dimethyl ammonium chloride (DDDM), tetradecyl dimethyl benzyl ammonium chloride ("DIBACTOL", manufactured by Huntington Labortories, Inc.) tetrabutyl ammonium hydrogen sulfate, and mixtures thereof.

The decontaminating composition is further comprised of an aqueous solution (the liquid component) of a nonvolatile alcohol and a surface active agent. The surface active agent may be a detergent, a surfactant or a combination thereof.

The preferred nonvolatile alcohols are polyhydric alcohols. Examples of suitable polyhydric alcohols are ethylene glycol, trimethylene glycol, propylene glycol, glycerine, butylene glycol, tetramethylene glycol, butyl carbitol and low molecular weight polyvinyl alcohols as well as various mixtures of the foregoing.

The surface active agent may be a detergent, a surfactant or, preferably, a combination of a detergent and a surfactant. Examples of suitable detergents are sodium hexametaphosphate and sodium pyrophosphate. The surfactant may be an anionic surfactant, a cationic surfactant, or a nonionic surfactant. The anionic surfactant may, for example, be a metal salt of a long chain aliphatic sulfonate or a metal salt of a long chain aliphatic acid. The cationic surfactants used in the practice of this invention are usually long chain aliphatic ammonium salts. Examples of nonionic surfactants are polyvinyl alcohol, polyvinyl pyrrolidone, ethylene-propylene block copolymers and ethoxylated octylphenol.

The amount of nonvolatile alcohol in the aqueous solution is within the range of from about 5 percent by volume to about 50 percent by volume. A nonvolatile alcohol content of about 15 percent by volume is preferred. The amount of surface active agent in the aqueous solution varies from about 0.05 percent by weight to about 1.2 percent by weight. A preferred range is from about 0.1 percent by weight to about 0.5 percent by weight of surface active agent. Especially preferred is an aqueous solution containing about 0.1 percent by weight to surface active agent. The surface active agent is preferably a mixture of a detergent and a surfactant. Finally, it is preferred that the positively charged phase-transfer agent (quaternary ammonium salts) be incorporated into the solution. The amount of quaternary ammonium salts in the aqueous solution is preferably in the range of from 50 ppm to 5% by weight. Especially preferred is an aqueous solution containing about 1% by weight of the quaternary ammonium salt.

The preferred liquid component of the decontaminating composition is an aqueous solution containing 15 percent by volume of a nonvolatile alcohol, and 0.2 percent by weight of the surfactant ethoxylated octylphenol marketed by Rohm & Haas under the trademark Triton X-100.

Preferably, the decontaminating composition is a mixture, on a weight basis, of about 3 parts aqueous solution to 1 part of the total of the dry components. However, this mixture can be as high as 10 parts aqueous solution to 1 part of the total of the dry components and as low as 1 part aqueous solution to 1 part of the total of the dry components.

These decontaminating compositions have been found to be active against a plethora of agents which are confronted in chemical warfare. In particular, these compositions are effective against: ethyl phosphorodimethylamidocyanidate; isopropyl methylphosphonofluoridate; pinacolyl methylphosphonofluoridate; bis (2-chloroelhyl) sulfide; 2, 2-dichloro triethylamine; N-methyl 2, 2 dichlorodethylamine; 1,2 bis (2 chloroethylthio) ethane and compounds having formulas similar to VX:

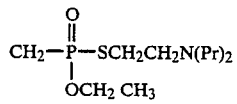

Figure 11:
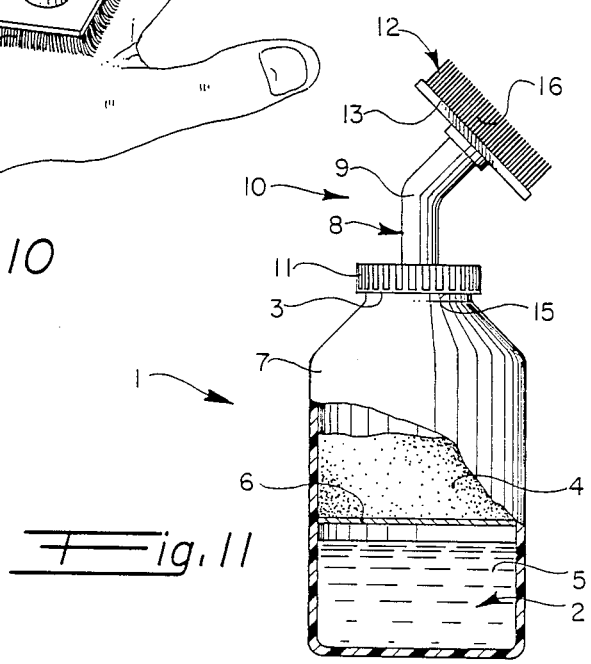
FIG. 11 depicts an alternate embodiment of the squeeze bottle dispenser delivery system of the present invention with part thereof in section to illustrate the components of the decontaminating composition being positioned in respective compartments separated by a frangible walls (seals).

Referring now to FIGS. 1 and 11, the dispensing system for the decontaminating composition is comprised of a substantially pliable thin-walled dispenser bottle 1 having an internal reservoir portion 2, and a threaded mouth portion 3 being, preferably, of reduced cross-section. Preferably, the internal reservoir portion 2 is further comprised of a dry component chamber (compartment) 4 and a liquid component chamber (compartment) 5. Positioned within the dry component chamber 4 are the compatible respective dry components of the decontamination composition. Similarly, positioned within the liquid component chamber 5 are the aqueous components of the decontamination composition. It should be noted that, as will be seen later, when the decontaminating composition is mixed, chamber 5 becomes the internal reservoir 2 therefor.

It is to be understood that if desired, alternatively a plurality of said chambers (compartments) like chamber 4, may be disposed in the bottle, each of said chambers (compartments) having a particular component of the decontaminating composition disposed therein.

The interface between the chambers 4 and 5 is comprised of a frangible wall 6. As shown in FIG. 1, chamber 4 is preferably comprised of a non-permeable sack positioned within the chamber 5 (the internal reservoir 2) of the bottle 1. Alternatively, and with particular reference to FIG. 11, the reservoir portion 2 can be laterally divided into the various chambers 4 and 5 by frangible wall 6 being substantially integral with the thin, pliable walls 7 of the dispenser bottle 1 itself.

Alternatively, if desired, the activator may be encapsulated in a water soluble polymer that is not easily oxidized. The preferred polymers in such a practice are polyvinyl alcohol and polyvinyl pyrrolidone (PVP).

Returning now to FIG. 1, the dispensing system is further comprised of an adapter 8 having a curved neck 9. Adaptor 8 is, at one end, removably, threadably fixed to the mouth portion 3 of the bottle 1. .

The curved shape of the neck of the adapter 8 permits the composition within the bottle to be easily and efficiently distributed therefrom onto the surface to be decontaminated.

The second other end of adapter 8 is threadably fixed to a spreading means 10.

Spreading means 10 is comprised of a threaded cap portion 11 and a spreading portion 12 being integral therewith. With reference now to FIGS. 2-4, spreading portion 11 is comprised of a lateral wall 13 having a plurality of apertures 14 formed therethrough. Cap portion 11 extends downwardly from the lateral wall 13. The internal walls of the cap portion 11 are threaded 15 so that the cap 11 may threadably engage the second opposite end of the adapter 8, thereby securing the cap 11 having the spreading portion 12 thereon in place over the curved neck of the adapter 8.

Integrally formed with the lateral wall 13 and extending outwardly therefrom is the spreading portion 12 of the spreading means 10. As illustrated, the spreading portion 12 is preferably formed of a plurality of brush hairs 16, if the decontaminating composition is formed as a cream. As will be understood by those skilled in the art, this spreading portion 12 could also be fabricated from a sponge if the decontaminating composition is formed as a liquid. Additionally, any other suitable means may be employed.

It should also be noted that, as illustrated, the spreading portion 12 is positioned being angled with reference to either the mouth 3 and/or the adapter 8. This angling is preferred in that it facilitates the flow of the decontaminating composition and further facilitates the even application thereof on a surface to be decontaminated.

With particular reference now to FIG. 4, positioned over the mouth portion 3 is a self-sealing valve means 17. Valve means 17 is preferably formed as a rubber disc sized to cover the said mouth portion 3. The disc has cross-hair gaps formed therein for permitting the controlled flow of the composition therethrough. In instances where the decontaminating composition is comprised having clay as a component (so as to be in the form of a cream), the cross-hairs are formed so as to be approximately 3/16 of an inch in length. In the case of where the decontaminating composition does not have clay as a component (so as to be in the form of a liquid), the cross-hairs are formed so as to be approximately ⅛ of an inch in length.

It should be noted that by providing a mouth portion 3 having a reduced cross-section, provides and increases the efficiency of the check valve means 17.

Finally, positioned over the aperture in the mouth portion is a thin, removable non-permeable seal 18. When in place, as described, seal 18 prevents any of the individual components, or any mixture thereof, from exiting the bottle 1, from either the internal reservoir 2 and/or either chamber 4 or 5. Removal of the seal 18 places the spreading means 10 in open communication with the contents of the bottle 1, so that the mixed decontaminating composition may exit from the reservoir 2 through the mouth portion 3 via apertures 14 where the mixed components are received on the spreading means 10 for dispensing on the surface to be decontaminated.

During shipment and storage and prior to use thereof, the components are maintained in their separate chambers 4 and 5. The liquid component and the dry components are maintained therein out of physical contact with one another by the frangible walls 6 which comprises the interface between the chambers 4 and 5.

Preferably, a stirring bar 19 (of FIG. 12) or marble 20 (FIG. 13) is also incorporated into the delivery system. This stirring bar aids in insuring that the decontaminating composition is throughly mixed and properly suspended for use. Preferably, this stirring bar is contained within the chamber which contains the "per-salt". Alternatively, it may be positioned within the chamber which contains the activator for hydrogen peroxide.

When the decontaminating composition is desired to be used, the individual applying the composition needs to threadably remove the adapter 8 from the bottle 1, so as to provide manual access to the seal 18. The seal 18 is then manually removed from the bottle 1 (FIG. 5). Once the seal 18 is removed, the adapter 8 may be threadably resecured on the bottle 1 (FIG. 6), whereby the composition and the delivery system therefor is readied for use. The user then squeezes the bottle dispenser 1. This pressure ruptures the frangible walls which separates the components, thereby allowing the said components to come into physical contact with one another (FIG. 7). The user then kneads and shakes the bottle 1, as required, to thoroughly mix the aforesaid components comprising the decontaminating composition (FIG. 8). At this time, the now mixed composition is retained in the reservoir 2.

With reference now to FIGS. 9 and 10, application of the decontaminating composition is made by gripping the bottle 1 (preferably by any portion located away from the mouth portion 3 thereof) and orienting the bottle 1, so that the mouth 3 and spreading means 10 is positioned lower than the internal reservoir portion 2. Oriented thusly, gravity causes the decontaminating composition to freely flow from the reservoir portion 2, through the mouth portion 3 and the cap portion 11 (through the apertures 14), respectively, where it is received on the spreading portion 12 of the spreading means 10. The spreading portion 12 is then brought into physical contact with the surface to be decontaminated, such as a wall (FIG. 8) or a hand (FIG. 9), thereby physically applying said decontaminant to the contaminated surface effecting the cleaning of the same.

While a specific embodiment of the present invention has been shown and described above to illustrate inventive principles, it is to be understood that such showing and description have been offered only by way of example and are not intended to be limiting. For example, it is to be understood that the delivery system could also be in the form of an elongated toothpaste type tube having a threaded mouth portion at one end and having the opposite end thereof being heat sealed. In any event, protection by letters patent of this invention in all its aspects as the same are set forth in the foregoing specification and drawings and in the appended claims is sought to the broadest extent that the prior art allows.

What is claimed is:

1. A decontaminating system comprising a hand-held portable container intended for ultimately dispensing a decontaminating composition, comprising, in combination, a bottle having a first compartment therein for storing dry components, the dry components including a water-soluble basic salt having hydrogen peroxide of crystallization, the dry components further including an activator for the hydrogen peroxide, the bottle further having a second compartment therein for storing liquid components, the liquid components including an aqueous solution of a non-volatile alcohol and further including a positively-charged phase transfer agent, means within the bottle for separating the first and second compartments, manually actuated means for combining the separated components, as desired, for mixing the dry and liquid components, thereby producing the decontaminating composition, and dispensing means carried by the bottle for dispensing the decontaminating composition.

2. The decontaminating system of claim 19, wherein:
the bottle is formed with pliable walls defining therebetween said second compartment, and the bottle further having a mouth portion;
spreading means carried by the bottle for receiving the composition exiting from the bottle through the mouth portion thereof, and further for spreading the received composition onto a surface in need thereof;
said first compartment being disposed in the second compartment of the bottle, and said first compartment having frangible walls.

3. The decontaminating system of claim 2, wherein the mouth portion is threaded.

4. The decontaminating system of claim 2, wherein the mouth portion is of reduced cross section.

5. The decontaminating system of claim 2, wherein the spreading means includes a cap portion received over the mouth portion of the bottle, said cap portion having at least one aperture formed therein, and said spreading means further including a spreading portion.

6. The decontaminating system of claim 5, wherein the spreading portion includes brush hairs for spreading the composition onto a surface in need thereof.

7. The decontaminating system of claim 5, wherein the spreading portion includes an absorbent material for spreading the composition onto a surface in need thereof.

8. The decontaminating system of claim 3, wherein the spreading means includes a threaded cap portion received over, and threadably engaging, the mouth portion of the bottle, such that the spreading means is threadably secured to said bottle.

9. The decontaminating system of claim 2, further including an adapter having a neck, one end of said neck being received over and secured to the mouth portion of the bottle, said neck further having a second end being secured to and in fluid communication with the spreading means, such that the composition may flow, respectively, through the mouth portion of the bottle and the neck of the adapter to be received in the spreading means.

10. The decontaminating system of claim 9, further including a cap portion positioned at the one end of the neck for being received over and secured to the mouth portion of the bottle, said cap portion having an aperture formed therein such that the composition may flow from the bottle into the neck of the adapter through, respectively, the mouth portion of the bottle and the cap portion, and wherein the spreading means further includes a lateral wall positioned at the second end of the neck of the adapter, said lateral wall having at least one aperture formed therein and further having the spreading portion disposed thereon, such that the composition in the neck of the adapter is in fluid communication with the spreading portion being received thereon for spreading the composition on a surface in need thereof.

11. The decontaminating system of claim 10, wherein the mouth portion of the bottle is threaded, and wherein the cap portion is threaded for threadably engaging the threads of the mouth portion, thereby securing said cap to said mouth portion.

12. The decontaminating system of claim 10, wherein the neck of the adapter is curved.

13. The decontaminating system of claim 10, wherein the spreading portion is comprised of a plurality of brush hairs.

14. The decontaminating system of claim 10, wherein the spreading portion is comprised of an absorbent material.

15. The decontaminating system of claim 2, further including a self-sealing valve positioned over the mouth portion of the bottle for controlling the flow of the composition therethrough.

16. The decontaminating system of claim 15, wherein the self-sealing valve is comprised of a rubber disc having a pair of intersecting cross-hair gaps formed therein.

17. The decontaminating system of claim 2, wherein the frangible walls are nonpermeable.

18. The decontaminating system of claim 1, wherein the second compartment comprises an internal reservoir formed by the walls of the bottle, and wherein the first compartment is contained within the reservoir, the first compartment comprising a chamber having frangible walls.

19. The decontaminating system of claim 1, wherein the water soluble basic salt having hydrogen peroxide of crystallization comprises sodium percarbonate.

20. The decontaminating system of claim 1, wherein the activator for the hydrogen peroxide comprises an iron bearing clay.

21. The decontaminating system of claim 20, wherein the iron bearing clay is selected from the group consisting of attapulgite, bentonite, kaolinite, montmorillonite, Christiania clay and mixtures thereof.

22. The decontaminating system of claim 1, wherein the non-volatile alcohol comprises a polyhydric alcohol selected from the group consisting of ethylene glycol, trimethylene glycol, propylene glycol, glycerine, butylene glycol, tetramethylene glycol, butyl carbitol and low molecular weight polyvinyl alcohols and mixtures thereof.

23. The decontaminating system of claim 1, wherein the positively-charged phase-transfer agent comprises a quaternary ammonium salt having a chain of carbon atoms of about 6 to 30 in length on the quaternary nitrogen.

24. The decontaminating system of claim 1, further including a surface active agent.

25. The decontaminating system of claim 24, wherein the surface active agent comprises a mixture of a detergent and a surfactant.

26. The decontaminating system of claim 25, wherein the surfactant is selected from the group consisting of anionic, cationic and nonionic surfactants.

27. The decontaminating system of claim 1, further including a stirring means disposed within the bottle for insuring that the decontaminating composition is thoroughly mixed and properly suspended for use.

28. The decontaminating system of claim 27, wherein the stirring means comprises a marble.

29. The decontaminating system of claim 27, wherein the stirring means comprises a stirring bar.

30. The decontaminating system of claim 27, wherein the stirring means is disposed in the second compartment.

31. A decontaminating system comprised of:
a decontaminating composition including a water soluble basic salt having hydrogen peroxide of crystallization, an activator for hydrogen peroxide which effects free radical formation, a positively-charged phase transfer agent and an aqueous solution having a nonvolatile alcohol and a surface active agent wherein said components are thoroughly mixed just prior to use;
a pliable bottle having a mouth;
a spreading means removably affixed to the mouth of bottle, such that the spreading means is in open communication with the contents of said bottle;
a plurality of compartments disposed in the bottle, a first of said compartments having the water soluble basic salt disposed therein, a second of said compartments having the activator for hydrogen peroxide disposed therein, a third of said compartments having the phase transfer agent disposed therein and a fourth of said compartments having the aqueous solution disposed therein;
each of said compartments having a frangible wall which when ruptured, allows the components to become thoroughly mixed prior to dispensing through the mouth of the bottle where it may be received on the spreading means where it may be spread by the spreading means over a surface to be decontaminated.

* * * * *